United States Patent [19]

Marrelli

[11] Patent Number: 5,101,164

[45] Date of Patent: Mar. 31, 1992

[54] PETROLEUM STREAM MONITORING SYSTEM AND METHOD WITH SAMPLE VERIFICATION

[75] Inventor: John D. Marrelli, Houston, Tex.

[73] Assignee: Texaco Inc., White Plains, N.Y.

[21] Appl. No.: 584,679

[22] Filed: Sep. 19, 1990

[51] Int. Cl.$^5$ .............................................. G01N 23/00
[52] U.S. Cl. ........................... 324/640; 73/61.1 R; 137/172
[58] Field of Search .................. 137/118, 119, 172; 73/61.1 R; 324/640

[56] References Cited

U.S. PATENT DOCUMENTS

| 3,253,711 | 5/1966 | Young | 137/172 X |
| 3,966,603 | 6/1976 | Grant | 137/172 X |
| 4,064,893 | 12/1977 | Pitt | 137/119 X |
| 4,301,400 | 11/1981 | Papp | 324/606 |
| 4,647,371 | 3/1987 | Schmitt | 137/172 X |
| 4,947,127 | 8/1990 | Helms | 324/640 |
| 4,947,128 | 8/1990 | Halton | 324/460 |

Primary Examiner—Alan Cohan
Attorney, Agent, or Firm—Robert A. Kulason; James J. O'Loughlin; Ronald G. Gillespie

[57] ABSTRACT

A multiphase petroleum stream monitoring system and method includes withdrawing a first sample stream from the petroleum stream. Both sample streams are irradiated with microwave energy. A second sample stream is withdrawn from the petroleum stream. Microwave energies that have passed through the sample streams are received. A signal circuit generated signals corresponding to an electrical property of the sample stream in accordance with the received microwave energies. A computer determines the validity of the sample streams and provides a water cut data on the petroleum stream when sample streams are valid sample streams.

8 Claims, 1 Drawing Sheet

PETROLEUM STREAM MONITORING SYSTEM AND METHOD WITH SAMPLE VERIFICATION

BACKGROUND OF THE INVENTION

Field of the Invention

The present invention relates to water cut monitoring and methods in general and, more particularly, to a microwave water cut monitoring system and method.

SUMMARY OF THE INVENTION

A multiphase petroleum stream monitoring system and method includes withdrawing a first sample stream from the petroleum stream. Both sample streams are irradiated with microwave energy. A second sample stream is withdrawn from the petroleum stream. Microwave energies that have passed through the sample streams are received. A signal circuit generated signals corresponding to an electrical property of the sample stream in accordance with the received microwave energies. A computer determines the validity of the sample streams and provides a water cut data on the petroleum stream when sample streams are valid sample streams.

The objects and advantages of the invention will appear more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the invention.

DESCRIPTION OF THE INVENTION

Figure 1:
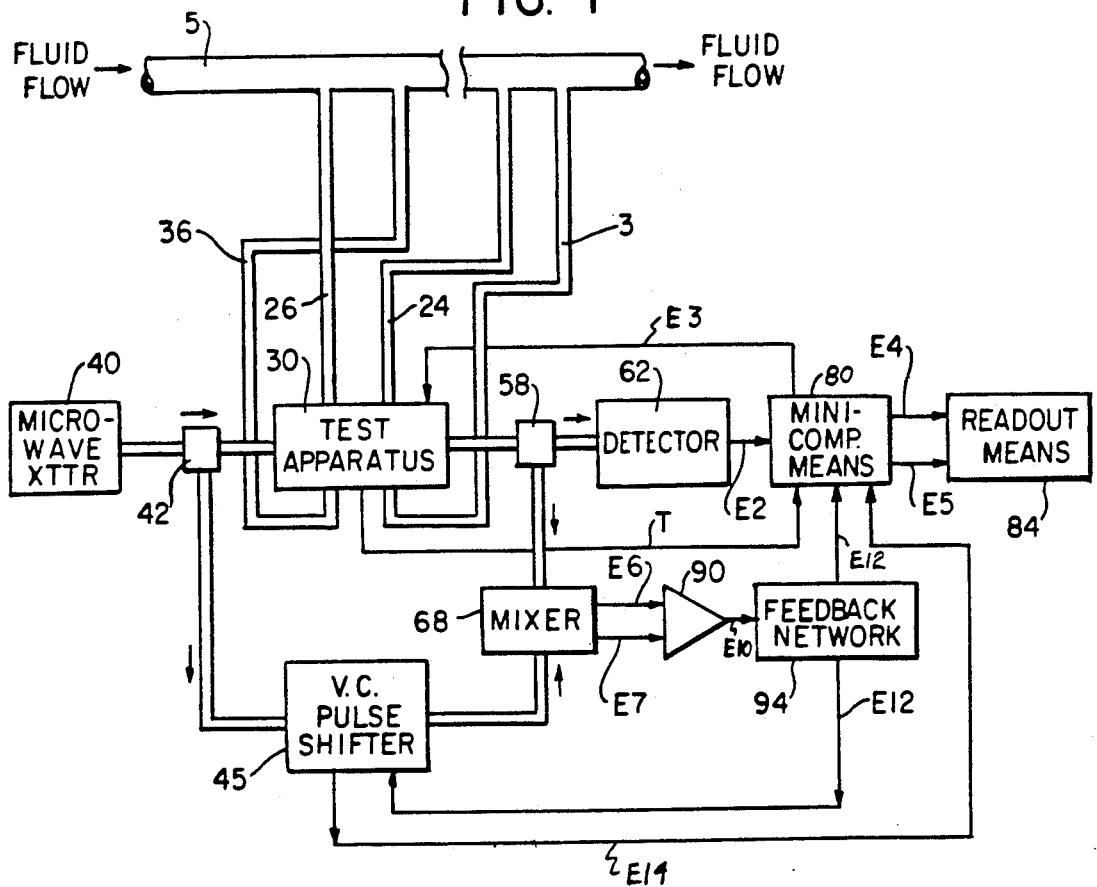
FIG. 1 is a partial simplified block diagram and a partial schematic of a petroleum stream monitoring system constructed in accordance with the present invention.

Referring to FIG. 1, there is shown a pipeline 5, carrying a flowing petroleum stream, having sampling lines 24 and 26, respectively, which draw off sample streams and provide them to test apparatus 30. The broken lines in pipeline 5 indicate that sampling lines 24 and 26 may be placed any desired distance apart.

Test apparatus 30 will be described in more detail hereinafter. Sufficient to say at this time that the sample streams in sampling lines 24 and 26 pass through test apparatus 30 and enter sampling lines 34 and 36, respectively, which are in turn connected to pipeline 15.

While the sample streams are flowing through test apparatus 30, they are subjected to microwave analysis. In this regard a microwave transmitter 40 provides electromagnetic energy, hereinafter referred to as microwave energy, at a microwave frequency. Transmitter 40 is low powered and may use a microwave gun source. Transmitter 40 provides the microwave energy to a directional coupler 42. Directional coupler 42 provides the microwave energy to a conventional type voltage control phase shifter 45 and to test apparatus 30. All conductance or carrying of microwave energy is accomplished by using conventional type wave guides and coaxial cables.

The microwave energy, after passing through a sample stream exits test apparatus 30 and is hereinafter referred to as test microwave energy. The test microwave energy is applied to a directional coupler 58. Directional coupler 58 provides the test microwave energy to a detector 62 and to a mixer 68.

Detector 62 provides a signal E2, corresponding to the test microwave energy, to minicomputer means 80. It should be noted at this time, as will be explained hereinafter, that there is microwave switching within test apparatus 30 that in effect causes signal E2 to be a time divided multiplex signal, that is, at one point in time signal E2 represents the ,test microwave energy associated with the sample stream in lines 26 and 36 and that at another time, signal E2 corresponds to the test microwave energy associated with sample fluid flowing in lines 24 and 34. Obviously these times are-alternating constantly during testing. Signal E2 is provided to minicomputer means 80 which provides signal E3 to control test apparatus 30.

There is a temperature sensing device within test apparatus 30 which provides a temperature signal T, corresponding to the sensed temperature of the sample streams, to computer means 80. Computer means 80 provides two signals E4 and E5 corresponding to the water cuts of the sample stream flowing in line 24 and to sample stream flowing in line 26, respectively. Signals E4 and E5 are provided to readout means 84.

Voltage control phase shifter 45 provides microwave energy, hereinafter called the reference microwave energy, to mixer 68, which mixes the reference microwave energy and the test microwave energy to provide two electrical signals E6 and E7, representative of the phases of the reference microwave energy and the test microwave energy, respectively.

A differential amplifier 90 provides an output E10 in accordance with the difference between signals E6, E7, to feedback network 94. Signal E10 is a function of the phase difference between the reference microwave energy and the test microwave energy. Feedback network 94 provides a signal E12 to minicomputer means 80 and to shifter 45, controlling the phase of the reference energy, and to minicomputer means 80. Signal E12, decrease e until there is substantially 90° phase difference the reference microwave energy and the test microwave energy. Voltage control phase shifter 45 indicates the amount of phase shift required to eliminate the phase difference. microwave energy. Voltage control phase shifter 45 indicates the amount of phase shift required to eliminate the phase difference.

Phase shifter 45 also provides a signal E14 to computer means 80 to signals T, E12 and E2 to select the proper water cut the particular sample stream.

Figure 2:
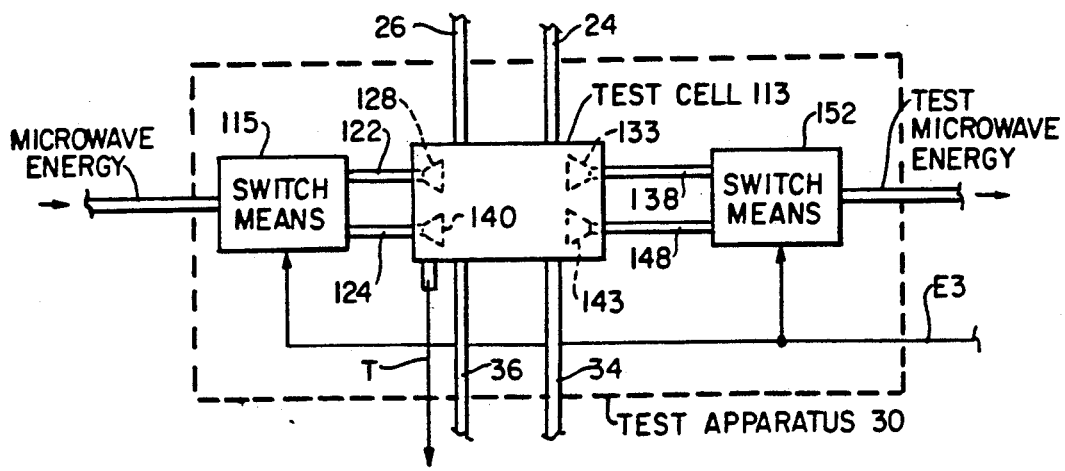
FIG. 2 is a simplified block diagram of the test apparatus shown in FIG. 1.

With reference to FIGS. 1 and 2, test apparatus 30 includes a Test cell 113,is of the type described and disclosed U.S. Pat. No. 4,947,127 issued Aug. 7, 1990. Microwave energy from directional coupler 42 enters switch 118 which provides microwave energy to test cell 113 through a line 122 or line 124. Line 122 provides the microwave an antenna 128 which radiates the microwave energy into stream flowing through lines 26, 36. The microwave energy passing through that sample stream is received by an antenna provides the received microwave energy to waveguide 138.

Similarly, the microwave energy in line 124 is provided to an antenna which transmits the microwave energy into the sample stream through lines 24 and 34. The microwave energy that through that sample fluid is received by antenna 143 a to a waveguide 148. Wave-guides 138 and 148 are connected to switch means 152 which is controlled by signal E3. The output of switch means 152 is the test microwave energy and is provided to directional coupler 58. Signal E3 controls switch means 118 and 152 so that during one time frame the microwave energy is being transmitted through the sample stream in lines 26 and 36 and during a second time frame the microwave energy is being transmitted through the sample stream in lines 24, 34.

The present invention, as described hereinbefore, provides for sample verification. All conventional type water cut monitors make a basic assumption that the petroleum stream will remain the same as at the point of monitoring. That is the flow regime will not change and therefore the monitoring is accurate. The flow regime changes are not known until the present invention. Thus, if the flow regime changes significantly the sample streams in lines 24 and 26 will differ significantly and invalidate the determined water cuts.

What is claimed is:

1. A multiphase petroleum stream monitor comprising:
   first sample stream means for withdrawing a first sample stream from the petroleum stream at a first location,
   second sample stream means for withdrawing a second sample stream from the petroleum stream at a second location,
   irradiating means for irradiating both sample streams with microwave energy,
   receiving means for receiving microwave energies that have passed through both sample streams,
   signal means connected to the receiving means for providing signals corresponding to an electrical property of the sample streams in accordance with the received microwave energies, and
   means for providing a validated water cut signal corresponding to the water cut of the petroleum stream in accordance with the signals from the signal means.

2. A monitor as described in claim 1 in which the means for providing a validated water cut signal will not provide a validated water cut signal when the water cut of the two sample streams differ significantly.

3. A system as described in claim 2 in which the irradiating means includes:
   source means for providing microwave energy,
   a first plurality of antenna means for irradiating microwave energy, and
   first switching means connecting the source means to the plurality of antenna means for providing microwave energy from the source means to each antenna means at different times so that each antenna means irradiates a corresponding sample stream with microwave energy.

4. A system as described in claim 3 in which the detecting means includes:
   a second plurality of antenna means, each antenna means being means for receiving microwave energy,
   second switching means, connected to the second plurality of antenna means and cooperating with the first switching means, for passing microwave energy from the second plurality of antenna means as test microwave energy to the signal means.

5. A multiphase petroleum stream monitoring method comprising the steps:
   withdrawing a first sample stream from the petroleum stream at a first location,
   withdrawing a second sample stream from the petroleum stream at a second location,
   irradiating both sample streams with microwave energy,
   receiving microwaves energies that have passed through both sample stream,
   providing signals corresponding to an electrical property of the sample streams in accordance with the received microwave energies, and
   providing a validated water cut signal corresponding to the water cut of the petroleum stream in accordance with the signals from the signal means.

6. A monitor as described in claim 5 in which the validated signal step include providing the validated water cut signal when the water cut of the two sample streams do not differ significantly.

7. A method as described inn claim 6 in which the irradiating step includes:
   providing microwave energy,
   irradiating microwave energy with a first plurality of antenna means, and
   providing microwave energy from the source means to each antenna means at different times so that each antenna means irradiates a corresponding sample stream with microwave energy.

8. A method as described in claim 7 in which the detecting step includes:
   receiving microwave energy with a second plurality of antenna means,
   second switching means, passing microwave energy from each antenna means of the second plurality of antenna means at different times as test microwave energy to the signal means.

* * * * *